United States Patent [19]
Horwitz et al.

[11] Patent Number: 5,721,209
[45] Date of Patent: Feb. 24, 1998

[54] IRON CHELATOR AND INHIBITOR OF IRON-MEDIATED OXIDANT INJURY

[75] Inventors: Lawrence D. Horwitz, Engelwood; Marcus A. Horwitz, Los Angeles; Bradford W. Gibson, Berkeley; Joseph Reeve, Oakhurst, all of Calif.

[73] Assignee: The Regents of the University of California, Oakland, Calif.

[21] Appl. No.: 383,180

[22] Filed: Feb. 3, 1995

[51] Int. Cl.$^6$ .................................................. A61K 38/12
[52] U.S. Cl. .......................... 514/11; 514/17; 514/18; 530/317; 530/329; 530/330; 435/71.2; 435/118; 435/120; 435/863; 435/864; 435/865; 435/866; 540/524; 540/526
[58] Field of Search ........................ 514/11, 17, 18; 530/317, 329, 330; 435/863, 864, 865, 866, 71.2, 118, 120; 540/524, 526

[56] References Cited

PUBLICATIONS

Chemical Abstracts 108:218746, "Mycobactins and Exochelins", Barclay et al., 1988.
Chemical Abstracts 98:157511, "Iron–Binding Compounds", Barclay et al., 1983.
Kirschner, Richard and Gary Fantini, "Role of Iron and Oxygen–Derived Free Radicals in Ischemia–Reperfusion Injury," *Journal of The American College of Surgeons*, vol. 179, No. 1, pp. 103–117, (Jul. 1994).
Scheibel and Stanton, "Antimalarial Activity of Selected Aromatic Chelators. IV. Cation Uptake by *Plasmodium falciparum* in the Presence of Oxines and Siderochromes," *Molecular Pharmacology: An International Journal*, vol. 30, No. 4, pp. 364–369, (Oct. 1986).
Sharman, Williams, Ewing and Ratledge, "Isolation, purification and structure of exochelin MS, the extracellular siderophore from *Mycobacterium smegmatis*," *Biochemical Journal*, pp. 187–196, (Jan. 1, 1995).
Barclay, Raymond and Colin Ratledge, "Iron–Binding Compounds of *Mycobacterium avium, M. intracellulare, M. scrofulaceum*, and Mycobactin–Dependent *M. paratuberculosis* and *M. avium*," *Journal of Bacteriology*, pp. 1138–1146, (Mar. 1983).
Barclay and Ratledge, "Metal Analogues of Mycobactin and Exochelin Fail to Act as Effective Antimycobacterial Agents," *Zbl. Bakt. Hyg. A* 262, 203–207 (1986).
Barclay and Ratledge, "Mycobactins and Exochelins of *Mycobacterium tuberculosis, M. bovis, M. africanum* and Other Related Species," *Journal of General Microbiology*, 134, 771–776 (1988).
Byler, Richard M. et al., "Hydrogen peroxide cytotoxicity in cultured cardiac myocytes is iron dependent," *American Physiological Society*, (1994).
Fiss, Ellen H. et al., "Identification of genes involved in the sequestration of iron in mycobacteria: the ferric exochelin biosynthetic and uptake pathways," *Molecular Microbiology*, 14(3), 557–569 (1994).

Gibson, Bradford W. et al. "Iron–Binding Exochelins" from-*Mycobacterium Tuberculosis: Structure, Characterization and Drug Design*, In: Program of the Third International Symposium on Mass Spectrometry in the Health and Life Sciences (Sep. 13–18, 1994).
Hall, Richard Malcolm et al, "Exochelin–mediated Iron Uptake into *Mycobacterium leprae*," *International Journal of Leprosy*, vol. 51, No. 4, (1983).
Horwitz, Lawrence D. et al., "Marked Reduction in Myocardial Infarct Size Due to Prolonged Infusion of an Antioxidant During Reperfusion," *Circulation* 89:1792–1801, (Apr. 1994).
Kubica, George P. and Lawrence G. Wayne (Editors), *The Mycobacteria: A Sourcebook*, Published by Marcel Dekker, Inc., New York and Basel, Part A, pp. 606–627.
Lesnefsky, Edward J. et al., "Deferoxamine Pretreatment Reduces Canine Infarct Size and Oxidative Injury," *The Journal of Pharmacology and Experimental Therapeutcs*, vol. 253, No. 3, 1103–1109 (1990).
Macham, L.P. and Ratledge, "A New Group of Water–soluble Iron–binding Compounds from Mycobacteria: The Exochelins," *Journal of General Microbiology*, 89, 379–382 (1975).
Macham, Ratledge and Nocton, "Extracellular Iron Acquisition by Mycobacteria: Role of the Exochelins and Evidence Against the Participation of Mycobactin," *Infection and Immunity*, vol. 12, No. 6, pp. 1242–1251 (Dec. 1975).
Ratledge, C., "Iron metabolism in Mycobacterium," *Iron Transport in Microbes, Plants and Animals*, pp. 207 233 (1987).
Sritharan, M. and Colin Ratledge, "Co–ordinated expression of the components of iron transport (mycobactin, exochelin and envelope proteins) in *Mycobacterium neoaurum*," *FEMS Microbiology Letters*, 60 (1989) 183–186.
Stephenson, Maris C. and Colin Ratledge, "Specificity of Exochelins for Iron Transport in Three Species of Mycobacteria," *Journal of General Microbiology*, 116, 521–523 (1980).
Wheeler, PR and C Ratledge, "Metabolism in Mycobacterium leprae, M. tuberculosis and other pathogenic mycobacteria," *British Medical Bulletin*, vol.44, No. 3, pp. 547–561 (1988).

*Primary Examiner*—Frederick Krass
*Attorney, Agent, or Firm*—Michael J. Ram; Marvin H. Kleinberg; Marshall A. Lerner

[57] ABSTRACT

Exochelins can be used to prevent damage to living tissue from the formation or presence of the (•OH) radical. In particular, the invention is directed to the administration of exochelins to infarcted myocardium prior to or coincidental with reperfusion to prevent damage to myocardium from iron mediated free radical formation. Also presented is the chemical structure of exochelins and modified exochelins as well as other applications of these materials in the treatment and diagnosis of disease in mammals.

13 Claims, 7 Drawing Sheets

FIG. 1A
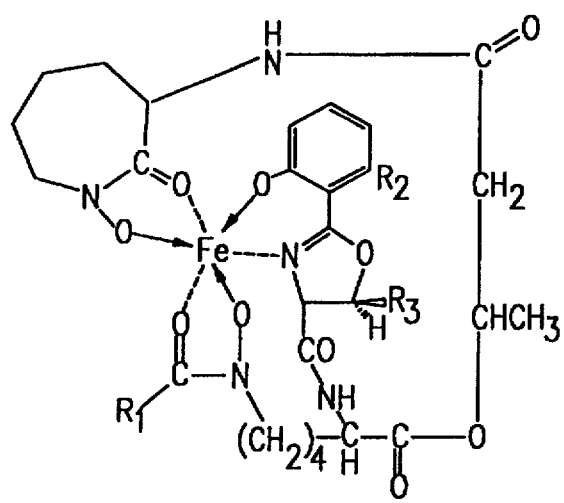
FERRIEXOCHELIN
FIG. 1B
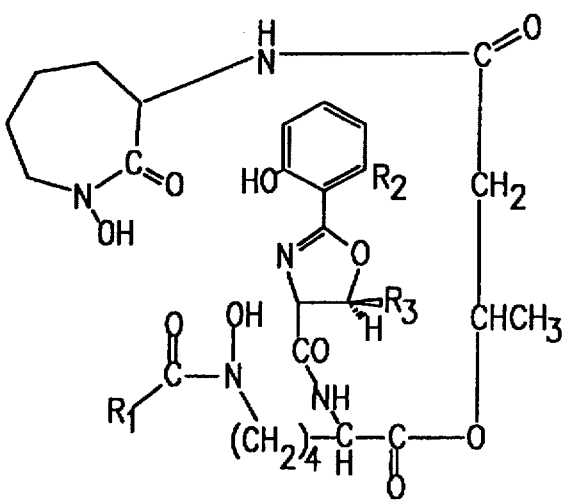
DESFERRIEXOCHELIN
| $R_1$ | | $R_3$ | $M_r$ |
|---|---|---|---|
| $(CH_2)_N COOCH_3$ | N=1–7 | H, $CH_3$ | 716–828 |
| $(CH_2)_x CH=CH(CH_2)_y COOCH_3$ | x+y=1–5 | H, $CH_3$ | 742–826 |
FIG. 1C (A) EXOCHELIN SATURATED SERINE SERIES

IRON CHELATOR AND INHIBITOR OF IRON-MEDIATED OXIDANT INJURY

BACKGROUND

The present invention relates to the chemical structure of a previously unidentified series of high affinity, iron-binding compounds, referred to by prior investigators as exochelins, which are released by mycobacteria. The invention also relates to modifications to these newly identified compounds to vary their physiological properties and applications of these newly identified and modified compounds.

In acute myocardial infarction, cardiac tissue is damaged by two sequential events, hypoxia in the ischemic phase and oxidative damage in the reperfusion phase. Myocardium damaged in the ischemic phase can be salvaged by reintroduction of blood to the ischemic area. However, reperfusion can result in injury as a result of an inflammatory response in the reperfused tissue caused by the migration of leukocytes into the tissue and the production of reactive oxygen species. One of the most reactive species is the hydroxyl species (•OH) which is generated in the presence of iron and which results in cell death. Prevention of the formation of (•OH) will prevent lethal cell damage from this cause. It is known that the formation of (•OH) is dependent on the presence of free iron and that iron chelators will prevent reperfusion injury. For example, the iron chelator deferoxamine, when administered prior to reperfusion, prevents injury and reduces myocardial infarct size during coronary artery occlusion and reperfusion. However, reperfusion injury occurs rapidly after the reestablishment of blood flow to the ischemic myocardium.

The formation of the (•OH) radical is dependent on the presence of free iron; iron chelators can scavenge the free iron and thus render the iron unavailable to catalyze the hydroxyl radical formation. However, these prior known iron chelating materials either do not prevent (•OH) production by the Fenton reaction (i.e., EDTA), or enter the cells too slowly (i.e., desferoxamine) such that sufficient quantities are not available to act rapidly enough to chelate enough iron to prevent the formation of (•OH) and the subsequent cell destruction. Desferoxamine has been demonstrated to be effective if administered prior to occurrence of the myocardial infarct but to be ineffective if administered at or after the onset of reperfusion.

Similar injury to heart tissue can occur as a result of heart bypass procedures, such as during open heart surgery, or to other body organs when they are deprived of oxygenated blood as a result of surgery or injury.

Exochelins were briefly described and their general function in the growth of mycobacteria was discussed by Macham, Ratledge and Barclay at the University of Hull in England (Lionel P. Macham, Colin Ratledge and Jennifer C. Nocton, "Extracellular Iron Acquisition by Mycobacteria: Role of the Exochelins and Evidence Against the Participation of Mycobactin", Infection and Immunity, Vol. 12, No. 6, p. 1242–1251, Dec. 1975; Raymond Barclay and Colin Ratlege, "Mycobactins and Exochelins of Mycobacterium tuberculosis, M. bovis, M. africanum and Other Related Species", Journal of General Microbiology, 134, 771–776, (1988); L. P. Macham and C. Ratledge, "A New Group of Water-soluble Iron-binding Compounds from Mycobacteria: The Exochelins", Journal of General Microbiology, 89, 379–282, (1975)). Macham identified the existence of a substance found in the extracellular fluid, which he referred to as exochelin. He described exochelin as a water and chloroform soluble compound which has the ability to chelate free iron. According to Macham, this material has similarities to mycobactin, which is located in the cell wall and functions to transmit iron to the interior of the cell. However, in contrast thereto, mycobactin is a lipophilic, water insoluble molecule which is unable to diffuse into, and assimilate free iron from, the extracellular environment. Macham et al recognized that exochelin functions at physiological pH to sequester iron from other iron bearing compounds in the serum, such as transferrin or ferritin, and present the iron in a form that can be transferred to mycobactin. Macham et al. did not isolate or purify the exochelins but identified them as a penta- or hexapeptide, having a molecular weight of 750 to 800, containing 3 mol of ε-N-hydroxylysine, εN-acetyl-εN-hydroxylysine, or εN-hydroxyornithine and 1 mol of threonine. Also, depending on the bacterial source of the exochelin, he disclosed that the molecules may also include β-alanine or salicylic acid.

Barclay (ibid). described the production of exochelins from twenty-two different strains of M. tuberculosis and related species. However, these prior investigators did not determine the specific structure of exochelins or identify any applications of the exochelins other than their function as a transport medium for iron to mycobactin located in the cell wall.

Thus there is a need for a substance that can be easily administered at the time of reperfusion and which will rapidly chelate the free iron as it is formed or made available to prevent the formation of the (•OH) radical. Further, there is a need to identify the specific structure of exochelin so that its function can be more fully understood and its utility as a diagnostic, treatment and preventive modality can be elucidated.

SUMMARY

These needs are met by the present invention which comprises the use of exochelins to prevent damage to living tissue from the formation or presence of the (•OH) radical. In particular, the invention is directed to the administration of exochelins to infarcted myocardium prior to or coincidental with reperfusion to prevent damage to myocardium from iron mediated free radical formation. Also presented is the chemical structure of exochelins and modified exochelins as well as other applications of these materials in the treatment and diagnosis of disease in mammals.

DRAWINGS

These and other features, aspects and advantages of the present invention will become better understood with reference to the following description, appended claims, and accompanying drawings, where:

FIG. 1 shows the chemical structure of an iron chelate of exochelin (ferriexochelin) and the desferriexochelin (iron free) molecule.

Figure 7:
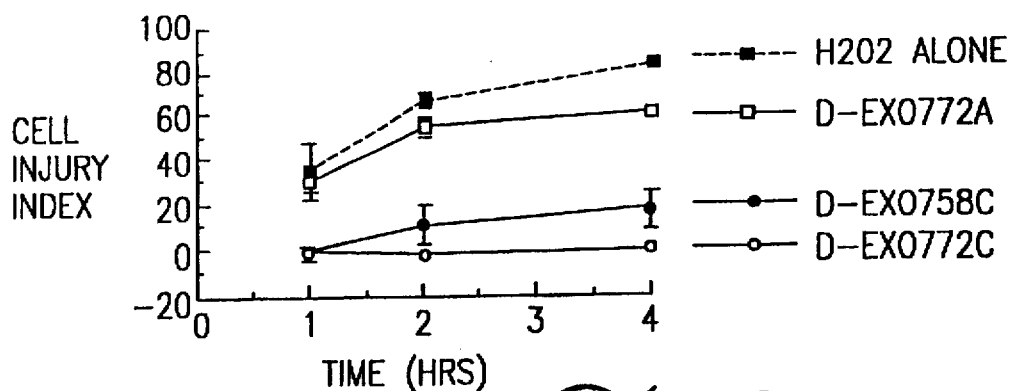
Figure 8:
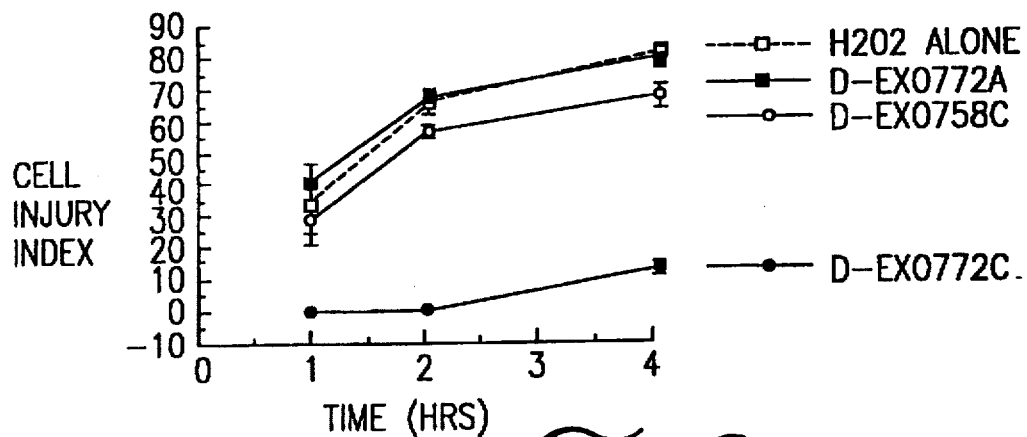
Figure 9:
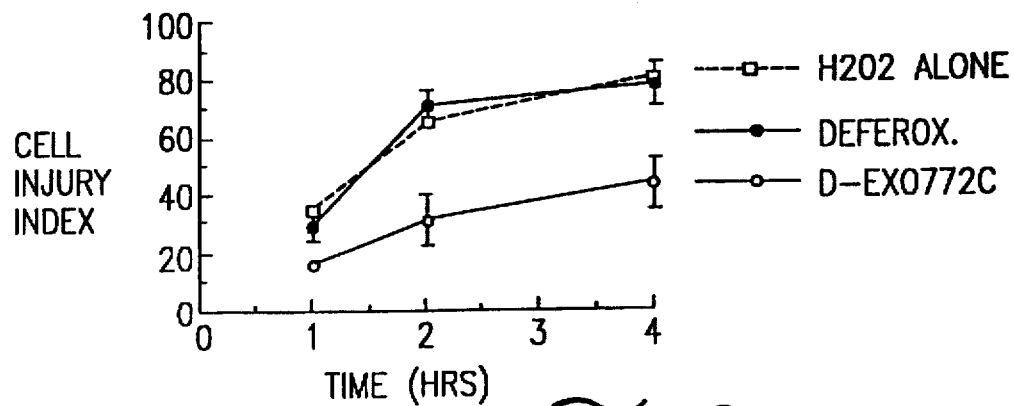

FIGS. 7, 8, and 9 are graphs comparing the inhibition of cell injury as a result of the use of exochelin 758C, 772A and 772C on cardiac myocytes.

Figure 10A:
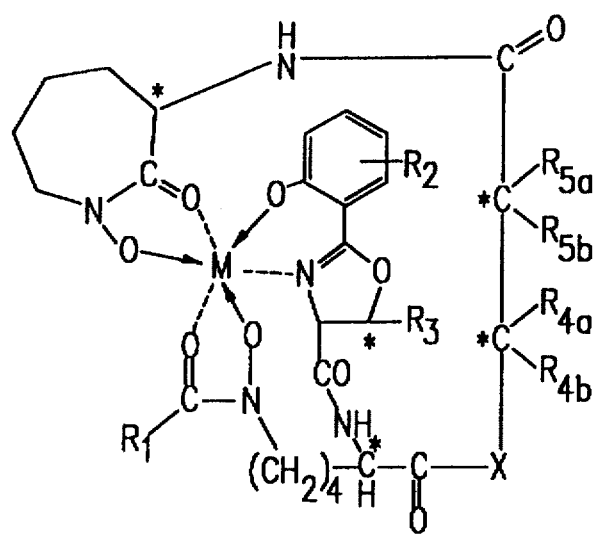
Figure 10B:
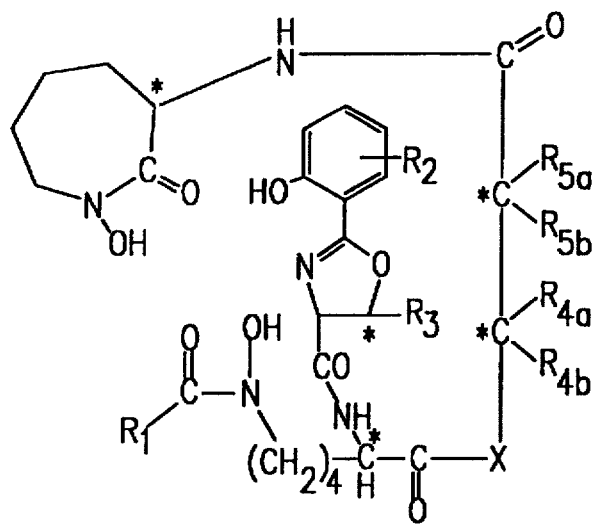

FIG. 10 shows the chemical structure of an iron chelate of exochelin (ferriexochelin) and the desferriexochelin (iron free) molecule with cites for modification identified.

DETAILED DESCRIPTION OF THE INVENTION

It has been found that exochelins can block, or significantly reduce, oxidative damage to tissue resulting from the iron-mediated catalysis of tissue/free radicals reactions, such as the hydroxyl radical (•OH), particularly hydroxyl radicals generated in the Fenton reaction, commonly referred to as reperfusion injury. It has been further found that the exochelins are effective to retard or prevent reperfusion injury when administered at the start of or concurrent with reperfusion. Additionally, it has been found that exochelins encompass a much broader class of materials and have a different chemical structure then originally theorized by Macham et al. and Barclay et al.

It has also been found that these materials can chelate a broad range of metals to result in materials not previously known. Besides preventing reperfusion injury, properly modified exochelins can be used to treat certain diseases, attack certain cells, such as cancer cells, and be used to monitor the effectiveness of drug treatment and detect the presence of certain disease states. In particular, it is known that the growth of neuroblastoma cells can be negatively affected by the removal of iron using the iron chelating compound desferrioxamine without similarly affecting the growth of normal cells. Other applications of exochelins include treatment of iron overload from transfusions or cancer chemotherapy, particularly for leukemia.

As a result of isolating and purifying exochelins, it has been found that exochelins are a family of molecules having a range of molecular weights and various different side chains. Further, purified exochelins have been prepared and their utility as scavengers of free iron, such that they are effective in preventing the formation of tissue damaging hydroxyl radicals (•OH), has been demonstrated for the first time. In particular, purified exochelins of *M. tuberculosis* have been isolated and have been shown to effectively remove iron from transferrin, lactoferrin and ferritin at physiological pH without transmitting any of the infectious properties of the bacteria from which they are derived. It has also been demonstrated for the first time that these exochelins block hydroxyl radical formation by the Fenton reaction and, based on the response of cardiac myocytes, can be effective to prevent reperfusion injury after myocardial infarction or vascular insults to other tissue when administered after the attach occurs as well as for several hours after the episode.

While mycobactins have been extensively studied, individual exochelins had not been isolated or purified and their structure and composition had not been previously defined. Further, we have found that prior references have mischaracterized the exochelins, and thus have failed to identify the structure of these compounds. In particular, Macham (ibid.) identified them as a penta- or hexapeptide, having a molecular weight of 750 to 800, containing 3 mol of $\epsilon$-N-hydroxylysine, $\epsilon$N-acetyl-$\epsilon$N-hydroxylysine, or $\epsilon$N-hydroxyornithine and 1 mol of threonine. We have found that the exochelins have a much broader range of molecular weights, constitute several series of compounds with an identifiable difference in molecular weights, include only 2 mol of $\epsilon$-N-hydroxylysine and are not peptides. A peptide is a polymer of an amino acid ($NH_2$—CHR—COOH) formed by the condensation of the carboxylic group of a first molecule with the amino group of another molecule to form an amide linkage (—CO—NH—). Exochelins can not be considered to be peptides. Instead, they contain three amino acids and other structural moieties (salicylic acid, dicarboxylic acids or monoester analogs, and hydroxy carboxylic acids) formed by amide (—NH—CO—), hydroxymate (—NH(OH)—CO—) and ester condensations (—CO—O—). The ferric and desferri forms are shown in FIG. 1.

Preparation

Exochelins were generated and purified from a virulent (Erdman) and avirulent (H37Ra) strain of *M. tuberculosis*. To enhance the production of *M. tuberculosis* exochelins the bacteria were cultured in an iron deficient medium. In particular, the Erdman strain of *M. tuberculosis* (American type culture collection 35801) and H37Ra (ATCC 25177) were grown on Middlebrook 7H11 agar plates at 37° C. in 5% $CO_2$. After 14 days the bacteria were harvested, suspended in 150 ml of modified Sauton's medium in culture flasks and incubated for 3 to 8 weeks. The modified Sauton's medium contained 0.12 mg/l ferric ammonium citrate without added surfactant.

Iron rich exochelins (ferriexochelins) were then recovered by filtering, saturating with iron and extracting with chloroform and purified by high pressure liquid chromatography (HPLC). Specifically, the supernatant fluid from the above suspension was filtered through successive 0.8 µm and 0.2 µm low-protein binding filters. The exochelins were then loaded with iron by saturating the filtered supernatant fluid by exposure to ferric chloride (150 mg per liter of culture filtrate). The ferric-exochelins were mixed with chloroform (1 volume of culture filtrate per 1.5 volumes of chloroform) and, after separation of the layers, the exochelin rich chloroform layer was removed and stored under anhydrous magnesium sulfate (2 g/l). The chloroform extract was then passed through a fritted glass filter and evaporated by rotary evaporation leaving behind a brown residue.

Figure 2A:
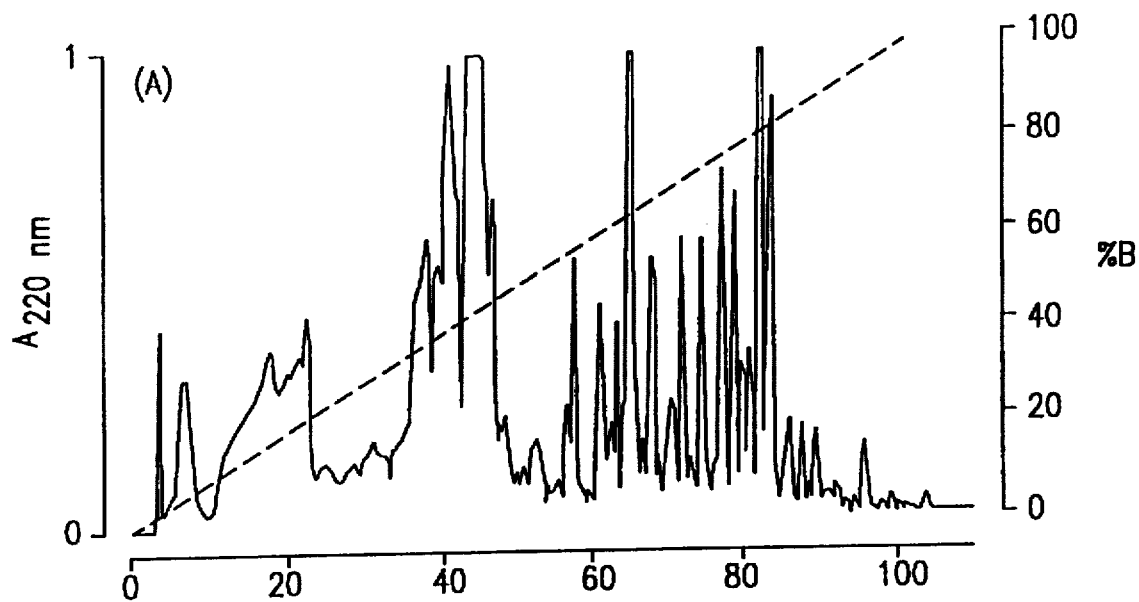
FIG. 2 shows an elution profile of a culture filtrate of M. tuberculosis monitored at 220 nm (FIG. 2A) and 450 nm (FIG. 2B).
Figure 2B:
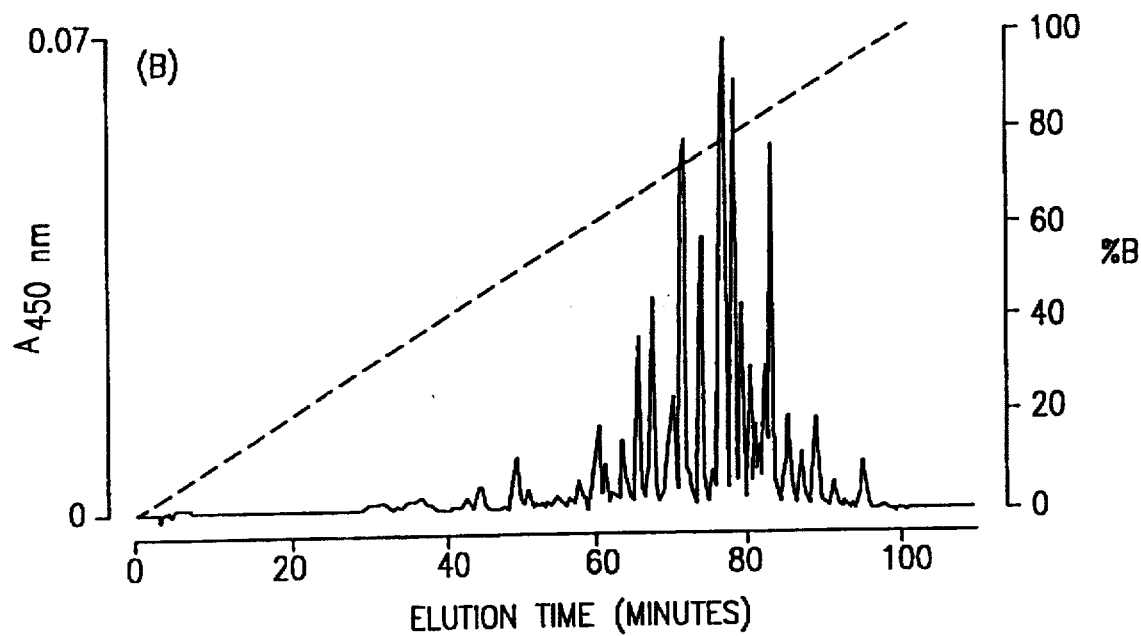

The brown residue was further purified by suspension in 5 ml of a first buffered solution (0.1% trifluoroacetic acid) which was introduced into a liquid chromatography column (C-18 Sep-Pak cartridge). The brown band which formed near the top of the column was eluted with a second buffer (0.1% TFA, 50% acetonitrile). The partially purified material was then diluted three-fold in 0.1% trifluoroacetic acid and subjected to reverse phase high pressure liquid chromatography at a rate of 1 ml/min followed by exposure to a C-18 column. The presence of the iron rich exochelins in the HPLC eluate was detected by simultaneous monitoring of the UV absorbance of the 450 nm peak (iron compounds) and the 220 nm peak which is indicative of amide and aromatic groups. Approximately 5 major and 10 minor peaks, shown in FIG. 2, eluted out of the final C-18 column exhibited a high 450/220 nm absorbance ratio. These were confirmed to be exochelins by mass spectrometry. Major peaks were further purified by a second reverse phase HPLC on an alkyl-phenyl column. The exochelins recovered from the Erdman strain of *M. tuberculosis* were identical to the exochelins recovered from the H37Ra strain.

Characterization

Based on LSIMS and ESI-MS analysis of the numerous peaks, in their ferri- ($Fe^{3+}$) form, eluted from the column (see FIG. 3), the iron-exochelins are not confined to the two specific molecules detailed above but include a family of species ranging in mass from 716 to 828 daltons. Each member of the family appears to differ from its neighbor by 14 daltons, reflecting the number of $CH_2$ groups in the $R_1$ alkyl side chain and/or 2 daltons, reflecting the presence of a double bond in the $R_1$ alkyl side chain. Accordingly, the exochelins appear to form two series with the subsequent members of each series differing in mass by 14 daltons, the saturated series having masses of approximately 663, 677, 691, 705, 719, 733, 747, 761 and 775 daltons and the unsaturated series having masses of 689, 703, 717, 731, 745, 759 and 775. Additionally, the presence or absence of a methyl group at $R_3$ (i.e., H or $CH_3$) further defines an additional two series of molecules referred to as the serine ($R_3$=H) and the threonine series ($R_3$=$CH_3$), as confirmed by amino acid analysis. The most polar compounds are to the left of the figure (elute earlier) and the least polar (most soluble in lipid) are to the right. However all the peaks are water soluble. Where more than one peak was found to have the same molecular weight each peak is further designated A, B or C (i.e., 758A, B and C) to indicate the level of polarity with A representing the more polar compound and the C representing the less polar form. The more polar forms are believed to result from a methyl groups attached at different location in the molecule.

Structure of the Exochelin

Figure 4A:
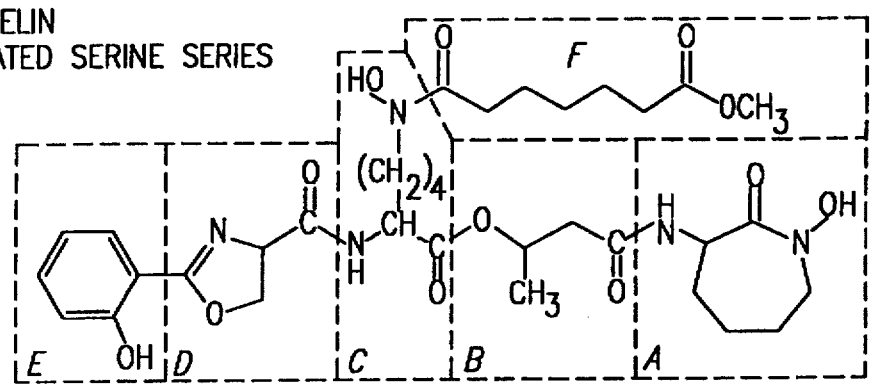
FIG. 4 shows the mass spectrometer spectra of a major serine-containing exochelin at m/z=720.3 along with the structure determined therefrom.
Figure 4B:
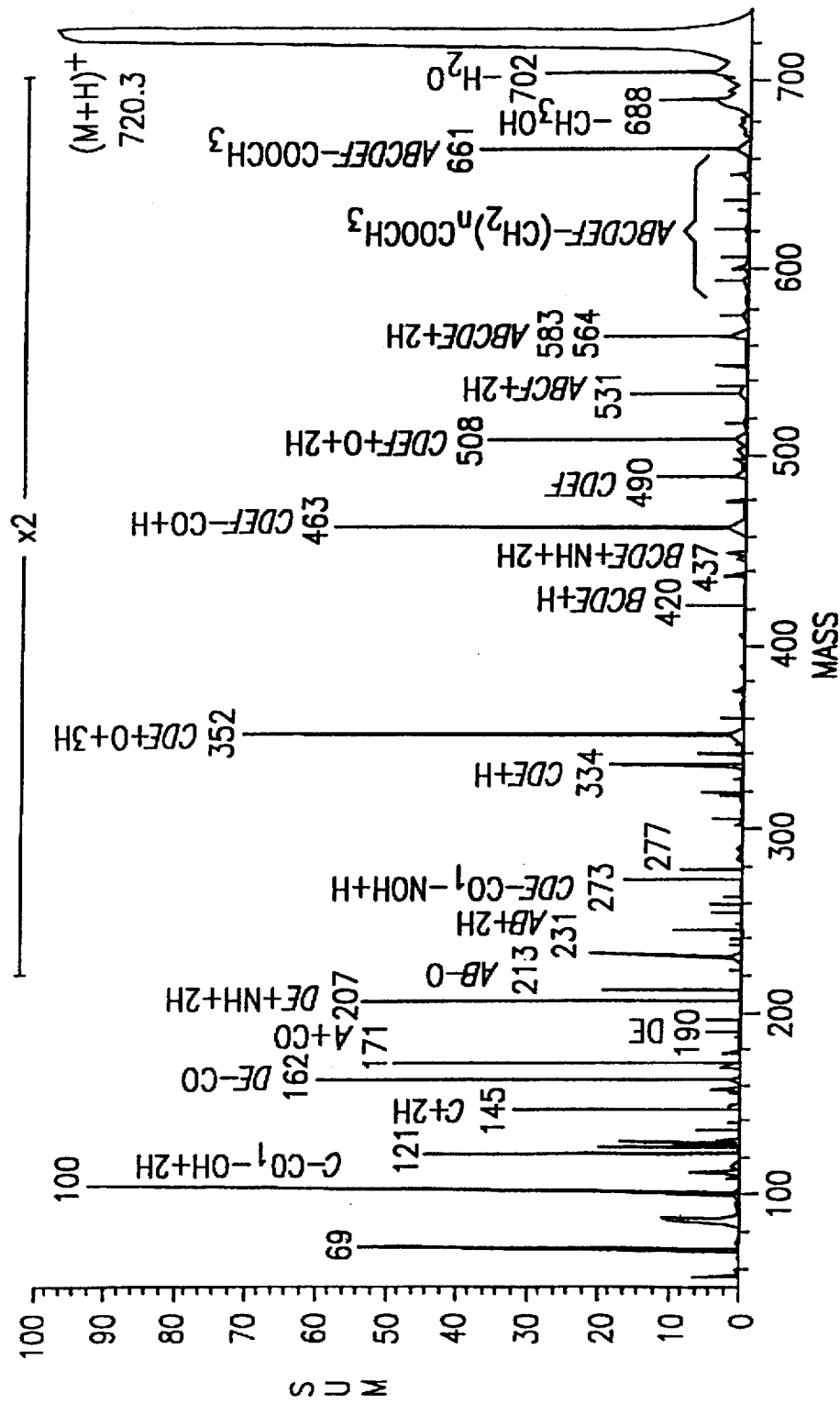

FIG. 4 shows the results of tandem mass spectrometric analysis under induced dissociation (He floated at 2 keV for a collision energy of 6 keV) of the major saturated serine-containing desferriexochelin with $(M+H)^+$ at m/z 720.3. The fragment ions were assigned to one of the six structural moieties A–F resulting from the cleavage products generated about the amide or ester bonds with the hydrogen transfer relative to the neutral molecule associated with each peak indicated on the spectrum shown in FIG. 4. Acid hydrolysis and methylation of the exochelins resulted in the formation of salicylic acid and pimelic acid. The mass spectrographic analysis indicates that the pimelic acid is present in the exochelin as a methyl ester.

Based on this analysis the general structure of the ferriexochelins and the desferriexochelins is shown in FIG. 1. The methyl group shown at the $R_4$ position (as defined in FIG. 10) may be in the $R_5$ position. The iron-exochelin core molecule is circular with iron in the center. It contains 3 amino acid moieties (two N-hydroxylysines and 1 serine or threonine, depending on whether $R_3$ is a hydrogen or methyl group). The major difference between exochelins and mycobactins of M. tuberculosis is that $R_1$ in the exochelins exists as either a saturated alkyl methyl ester $((CH_2)_NCOOCH_3)$ or a singly unsaturated alkyl methyl ester $(CH_2)_xCH$=$CH$ $(CH_2)_yCOOCH_3$ and exochelins have a much shorter alkyl side chain than mycobactins with these shorter side chains terminating in methyl ester moieties. These differences provide for the water solubility of the exochelins and their ability to function in the extracellular environment.

Clinical Utility

The clinical utility of the administration of exochelins to prevent reperfusion injury was demonstrated by application to adult rat myocytes.

Figure 3:
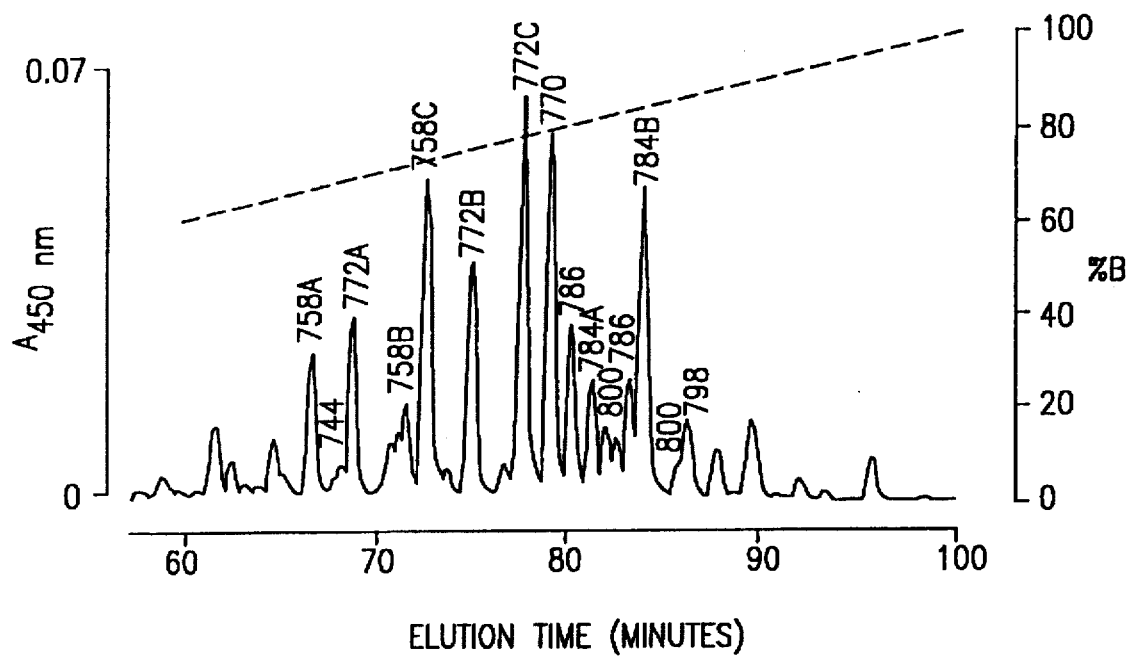
FIG. 3 shows an elution profile of the same filtrate monitored at 450 nm with the molecular weight of each peak shown.

In the Examples below the different exochelins, in both the desferri- and ferri- form, will be identified by the molecular weight as shown in the elution curve in FIG. 3.

EXAMPLE 1

The heart of a male rat was excised after the rat was anesthetized, a thoracotomy performed and the heart chilled in situ. The excised heart was then placed on a Langendorff apparatus and perfused with a collagenase and hyaluronidase in a 50 μM calcium in modified Krebs Ringer buffer solution. The tissue was then finely divided and dispersed in a collagenase/trypsin solution, filtered into a cold trypsin inhibitor solution and exposed to increasing concentrations of calcium. After removal of damaged cells, the remaining cell suspension was placed in several laminin-coated plastic dishes along with a culture medium containing 5% fetal bovine serum.

Figure 5:
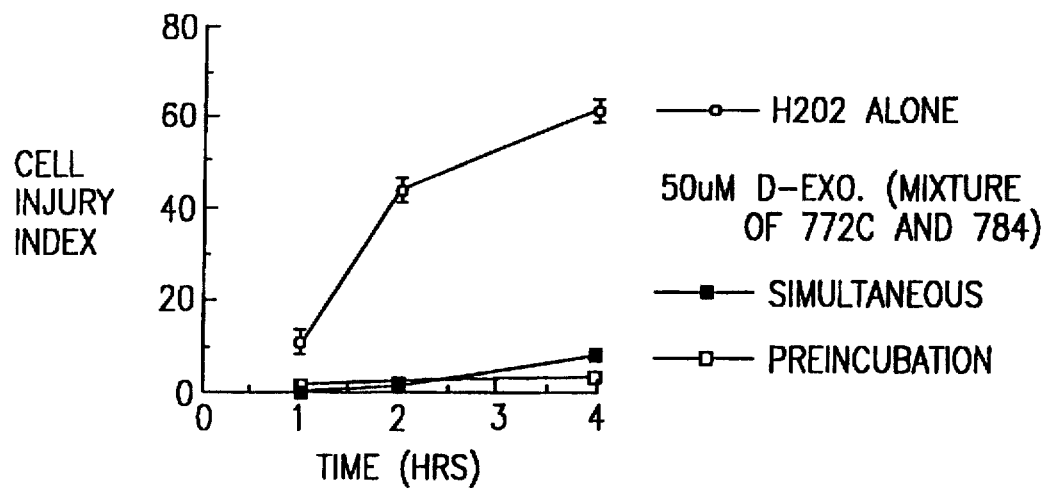
FIG. 5 is a graph showing the inhibition of cell injury as a result of the use of an exochelin mixture on cardiac myocytes.

After the cultures were allowed to sit for 48 hours hydrogen peroxide was added to each dish and the lactate dehydrogenase activity (LDH), which is indicative of cell injury, was measured at various time intervals. A cell injury index (CII) for comparison purposes was obtained by measuring the LDH in a nonexposed cell culture in both an as is condition (0 Index) and following exposure to a detergent that lyses 100% of the myocytes (1% Triton X-100) representing a CII of 100. The LDH under specified treatment conditions for various periods of time was then determined, the corresponding CII value determined and the individual results were plotted against time (FIG. 5).

Using the procedure described above, a mixture of the desferri-form of exochelins 772C and 784 (a 50:50 mixture of the 772C peak and the 784 peak), a relatively non-polar substance, was isolated and used to treat cell cultures. The exochelin were converted to the desferriexochelin form by incubation for several days with 50 millimolar EDTA at pH 6. The desferri- form was then repurified by chloroform extraction.

Three samples of cells were exposed to either a) $H_2O_2$, b) $H_2O_2$ and 50 μM of desferriexochelin (iron free exochelin) added simultaneously or c) $H_2O_2$ added 2 hours after addition of 100 μM of desferriexochelin to the cell culture (preincubation). The untreated cell cultured showed almost 62% cell injury over a 4 hour period. In contrast thereto, addition of exochelin simultaneously with, or 2 hours prior to, peroxide addition substantially prevented or significantly reduced cell damage, the cell injury being approximately 2 to 9%.

EXAMPLE 2

Figure 6:
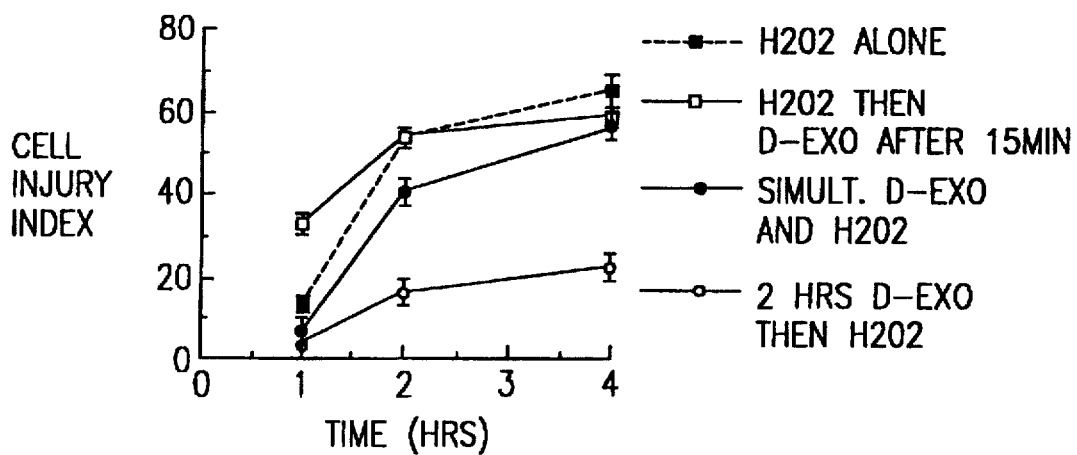
FIG. 6 is a graph showing the inhibition of cell injury as a result of the use of exochelin 758C on cardiac myocytes.

The procedure of Example 1 was repeated with desferriexochelin 758C which is relatively more polar than exochelins 772C and 784. There was little or no difference between the effect when desferriexochelin 758C was delivered along with or within 15 minutes of delivery of $H_2O_2$. In both instances after 2 hours the cell destruction was substantially the same as in the control. However, delivery of the desferriexochelin 758C 2 hours prior to $H_2O_2$ introduction cut the cell destruction to a CII of about 20. The results are shown in FIG. 6.

EXAMPLE 3

The procedure set forth above was repeated using desferriexochelin 772A, 772C and 758C. Plotted in FIGS. 7–9 are the results for 2 hour predelivery, simultaneous delivery and 20 minute delayed delivery of the exochelins. Only exochelin 772C shows retardation of injury under all conditions while exochelin 772A is not effective under any conditions. On the other hand, exochelin 758C shows protection only if delivered 2 hours prior to peroxide introduction. It is therefor concluded that the relatively non-polar, more lipid soluble exochelins are effective when administered with or after formation of the (•OH) radical, i.e., after injury occurs; the more polar exochelins must be administered 1 to 2 hours prior to the free radical generating event such as part of a cardioplegia solution to prevent or reduce cell destruction.

EXAMPLE 4

The capacity of exochelins to compete for iron with host iron-binding proteins was determined by incubating desferriexochelin with solutions of transferrin, lactoferrin, or ferritin at 4:1 and 1:1 molar ratios of iron to exochelin. The conversion of the exochelin from its desferri- to its ferriform was then determined by reverse phase HPLC. Within one minute of exposure of desferriexochelin to 95% iron-saturated transferrin, the exochelin had started to pick up iron from the transferrin and within one hour the exochelin was fully saturated with iron. Iron was also readily removed from 40% iron-saturated transferrin, which approximates the iron level in transferrin as it exists in serum. Similar results were obtained when desferriexochelin was exposed to iron-saturated lactoferrin. Likewise, ferritin released iron to the exochelin but at a slower rate than other iron binding proteins.

It has been discovered that exochelins are very effective in scavenging free iron in a physiological system and withdrawing iron from iron bearing protein. In particular it has been found that exochelin effectively block the formation of the hydroxyl free radical (•OH) and thus significantly reduce or prevent the injury to ischemic tissue when circulation of blood to that tissue is reestablished with the higher molecular weight, less polar exochelins being more effective in preventing cell destruction. While the benefit to cardiac tissue has been demonstrated, the benefit of the use of exochelins following interruption of blood flow to other body organs, including but not limited to the brain, kidney, liver, lung, bowel, and skeletal muscle is now apparent.

Experimentation has shown that the affinity of the exochelins is not limited to iron but that other metals can be chelated, such as Na, K, Mn, Mg, Al and Zn. Therefore, the exochelins can be used to deliver to the body various desirable metals or chelate various undesirable metals within the body. Additionally, certain cells, including certain cancer cells are known to have a need for or affinity for certain metals. This can be utilized to deliver to that cell reactive compounds attached to the exochelins for destruction of the cell (chemotherapy) or to target a diseased organ with a beneficial drug bound to the exochelin. Conversely, since certain cancer cells have a high demand for iron, the desferriexochelins can be used to bind free iron, thus preventing iron delivery to the cancer cell, resulting in the destruction of the cancer cell.

While the structure of exochelins recovered from *M. tuberculosis* is shown in FIG. 1, it is known that other mycobacteria can generate exochelins and that these exochelins may have different structure and include different amino acids depending on the mycobacteria from which they are derived. However, all exochelins will behave in a similar manner and exist in similar series with subsequent members thereof having a similar progression of molecular weights. The effectiveness of the different members of the series will also depend on the relative polarity of the molecules. Therefore, the invention contemplates exochelins generated from other mycobacteria including, but not limited to, *M. tuberculosis, M. microti, M. bovis, M. africanum, M. kansasii, M. marinum, M. gastri, M. nonchromogenicum, M. terrae, M. trivale, M. realincense, M. shimoidei, M. gordonae, M. asiaticum, M. szulgai, M. simiae, M. scrofulaceum, M. avium, M. intracellulare, M. xenopi, M. ulcerans, M. haemophilum, M. farcinogenes, M. lepraemurium, M. paratuberculosis, M. chelonae* subsp. *chelonae, M. chelonae* subsp. *abscessus, M. fortuitum, M. chitae, M. senegalense, M. agri, M. smegmatis, M. phlei, M. thermoresistibile, M. aichiense, M. aurum, M. chubuense, M. duvalii, M. flavescens, M. gadium, M. givum, M. komossense, M. neoaurum, M. obuense, M. parafortuitum, M. rhodesiae, M. sphagni, M. tokaiense* or *M. vaccae*.

It is also contemplated that exochelins can be modified to affect their solubility properties, metal chelating ability or cellular absorption rates. Additionally, detection of modified exochelins or exochelin in their metal chelated state, using monoclonal antibodies or chemical analysis as diagnostic tools, by way of blood analysis, urinalysis, invasive or noninvasive instrumental techniques, to monitor progress of a disease state or effectiveness of treatment. In particular, referring to the structures of the metal containing and metal free compounds shown in FIG. 10, the following substitutions are contemplated:

$R_1 = (CH_2)_n CH_3$ as a linear or branched chain; $(CH_2)_n COOH$, a fatty acid; $(CH_2)_n COOR$, $(CH_2)_x CH = CH(CH_2)_y COOH$, $(CH_2)_y COOR$, a fatty acid ester where R is an alkyl group; $(CH_2)_n CONH_2$;

$R_2$ = a substitution at any of the 4 open ring sites of alkyl groups, sulfonamides, hydroxyl, halogen, acetyl, carbamyl, amines, $NO_2$ or any combination thereof;

$R_3$—the H (serine) or $CH_3$ (threonine) can be replaced by side chains found on β-hydroxy amino acids which are capable of forming cyclic oxazoline structures.

$R_{4a}$ and $R_{4b} = H$, $CH_3$ or other alkyl or substituted alkyl groups;

$R_{5a}$ and $R_{5b} = H$, $CH_3$ or other alkyl or substituted alkyl groups;

$X = O, NH, S, CH_2$;

M = mono-, di-, or trivalent metals such as Pb, Al, Cd, Ni, Ag, Au, As, Mg, Mn, Zn, Cu, Ru, Nb, Zr, Ta, V, Ga, Pt, Cr, Sc, Y, Co, Ti, Na, K;* represents chiral centers which may be R or S;The various hydroxyl groups (OH) involved in chelating the metal can be replaced by various functional groups, such as H or a halogen, to vary the affinity of the compound for the chelated metal or to convert the molecule into a metal antagonist.Although the present invention has been described in considerable detail with reference to certain preferred versions and uses thereof, other versions and uses are possible. For example, exochelins can be used to attack infectious bacteria, such as *M. tuberculosis*, by blocking access of the mycobacteria to iron, to remove toxic levels of metals from the body or to deliver desirable metals to the body. Further, modified metal containing exochelins can deliver appended active drugs or chemicals to cites in the body which preferentially absorb the chelated metal and preferentially absorbed exochelins with chelated metals can be used as targets for treatment by other modalities, such as microwave energy for hypothermia treatment of cancer cells. Therefore, the spirit and scope of the appended claims should not be limited to the description of the preferred versions contained herein.

What is claimed is: 1. A composition for protecting live tissue in a mammal from injury resulting from exposure to the hydroxyl free radical formed following reestablishment of fluid flow to a body organ after restriction of blood flow to that body organ comprising an effective amount of a lipid and water soluble desferriexochelin, said amount being effective to protect said mammal upon the reestablishment of flow of fluid to the tissue. 2. A composition for preventing injury to living tissue in a mammal from the presence of iron mediated, hydroxyl radical formation comprising an effective amount of at least one compound of the formula:

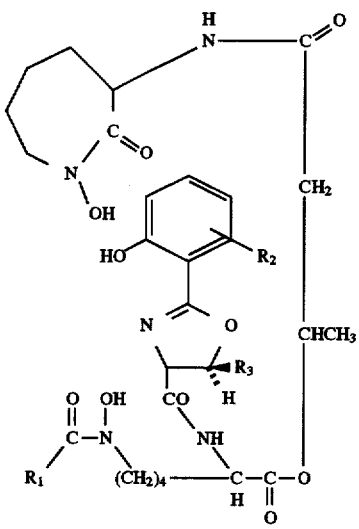

wherein $R_1$ is selected from the group consisting of $(CH_2)_N COOCH_3$ and $(CH_2)_x CH=CH(CH_2)_y COOCH_3$ with N being from 1 to 7 and x+y being from 1 to 5, $R_2$ is a chemical moiety substituted at any of the 4 open sites on the ring, said chemical moiety being selected from the group consisting of alkyl groups, sulfonamides, hydroxyl, halogen, acetyl, carbamyl, amines and $NO_2$ and combinations thereof, and $R_3$ is selected from the group consisting of H and $CH_3$ said compound having a molecular weight of from about 663 to 775.

3. A isolated compound having the formula:

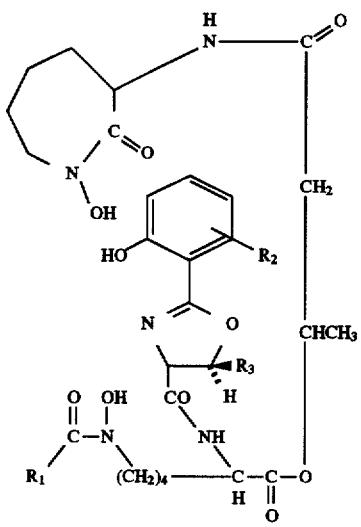

wherein $R_1$ is selected from the group consisting of $(CH_2)_N COOCH_3$ and $(CH_2)_x CH=CH-(CH_2)_y COOCH_3$ with N being from 1 to 7 and x+y being from 1 to 5, $R_2$ is a chemical moiety substituted at any of the 4 open sites on the ring, said chemical moiety being selected from the group consisting of alkyl groups, sulfonamides, hydroxyl, halogen, acetyl, carbamyl, amines and $NO_2$ and combinations thereof and $R_3$ is selected from the group consisting of H and $CH_3$, said compound having a molecular weight of from about 663 to about 775 daltons.

4. The composition of claim 2 wherein the composition includes a mixture of desferriexochelins having a molecular weight of 719 and 731 daltons.

5. The composition of claim 2 wherein the composition includes a mixture of relatively nonpolar desferriexochelins characterized by N being a whole number from 5 to 7.

6. The composition of claim 2 wherein the composition includes a mixture of relatively nonpolar desferriexochelins characterized by x+y being 4 or 5.

7. A composition for delivering an active compound to a mammal to treat a medical condition caused by the formation or presence of hydroxy free radicals, said composition comprising a compound of the formula:

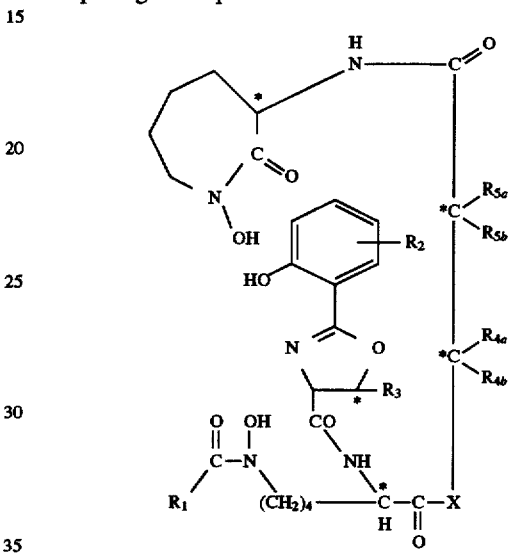

wherein $R_1$ is a chemical moiety selected from the group consisting of $(CH_2)_n CH_3$, $(CH_2)_n COOH$, $(CH_2)_n COOR$, $(CH_2)_x CH=CH(CH_2)_y COOH$, $(CH_2)_x CH=CH(CH_2)_y COOR$, where R is an alkyl group and $(CH_2)_n CONH_2$ where n is from 1 to 7 and x+y is 1 to 5;

$R_2$ is a chemical moiety substituted at any of the 4 open sites on the ring, said chemical moiety being selected from the group consisting of alkyl groups, sulfonamides, hydroxyl, halogen, acetyl, carbamyl, amines and $NO_2$ and combinations thereof;

$R_3$ is a chemical moiety selected from the group consisting of H, CH, and side chains found on β-hydroxy amino acids which are capable of forming cyclic oxazoline structures; and $R_{4a}$, $R_4b$, $R_{5a}$, $R_{5b}$ are chemical moieties selected from the group consisting of H, alkyl groups and substituted alkyl groups and x is 0, NH, S or $CH_2$.

8. The composition of claim 7 wherein said compound is selected from the group consisting of saturated and unsaturated compounds, the saturated compounds having masses of 663, 677, 691, 705, 719, 733, 747, 761 or 775 daltons and the unsaturated compounds having masses of 689, 703, 717, 731, 745, 759 or 773 daltons.

9. A isolated metal chelate having the formula:

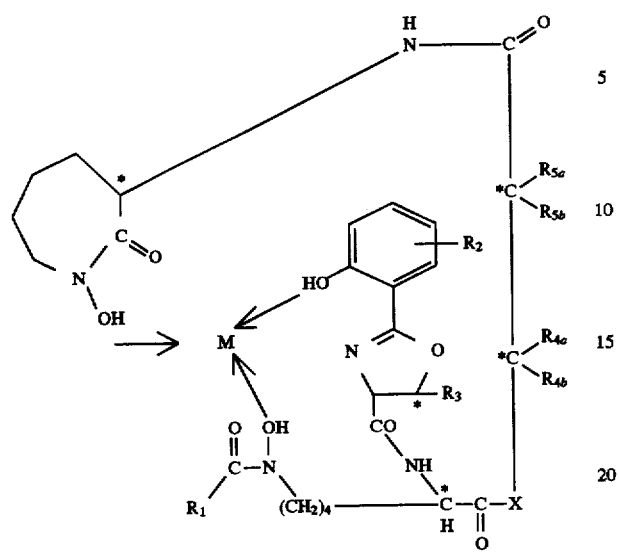

wherein
- $R_1$ is a chemical moiety selected from the group consisting of $(CH_2)_nCH_3$, $(CH_2)_nCOOH$, $(CH_2)_nCOOR$ $(CH_2)_xCH=CH(CH_2)_yCOOH$, $(CH_2)_xCH=CH(CH_2)_yCOOR$ where R is an alkyl group and $(CH_2)_nCONH_2$ n being from 1 to 7 and x+y is 1 to 5;
- $R_2$ is a chemical moiety substituted at any of the 4 open sites on the ring, said chemical moiety being selected from the group consisting of alkyl groups, sulfonamides, hydroxyl, halogen, acetyl, carbamyl, amines and $NO_2$ and combinations thereof;
- $R_3$ is a chemical moiety selected from the group consisting of H, $CH_3$ and side chains found on β-hydroxy amino acids which are capable of forming cyclic oxazoline structures; and
- $R_{4a}$, $R_{4b}$, $R_{5a}$, $R_{5b}$ are chemical moieties selected from the group consisting of H, alkyl groups and substituted alkyl groups; and
- M is selected from the group consisting of iron, lead, aluminum, cadmium, nickel, silver, gold, arsenic, magnesium, manganese, zinc, copper, rubidium, niobium, zirconium, tantalum, vanadium, gallium, platinum, chromium, scandium, yttrium, cobalt, titanium, sodium and potassium and x is O, NH, S or $CH_2$.

10. The metal chelate of claim 9 wherein M is iron.

11. A composition for protecting live tissue in a mammal from injury resulting from exposure to the hydroxyl free radical formed following reestablishment of fluid flow to a body organ after restriction of blood flow to that body organ comprising an effective amount of a lipid and water soluble desferriexochelin, said amount being effective to protect said mammal upon the reestablishment of flow of fluid to the tissue, said desferriexochelin being administered in a solution selected from the group consisting of reperfusion solution and cardioplegia solution.

12. A composition for protecting live tissue in a mammal from injury resulting from exposure to the hydroxyl free radical formed following reestablishment of fluid flow to a body organ after restriction of blood flow to that body organ comprising an effective amount of a compound having the formula:

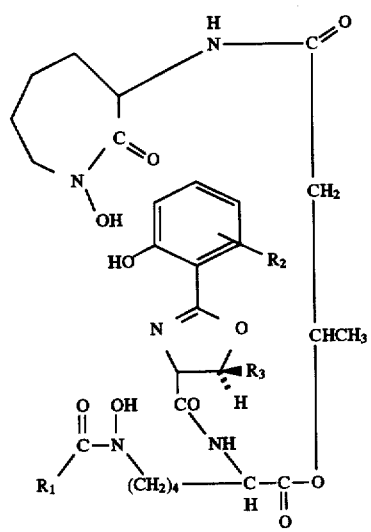

wherein $R_1$ is selected from the group consisting of $(CH_2)_NCOOCH_3$ and $(CH_2)_xCH=CH—(CH_2)_yCOOCH_3$ with N being from 1 to 7 and x+y being from 1 to 5, $R_2$ is a chemical moiety substituted at any of the 4 open sites on the ring, said chemical moiety being selected from the group consisting of alkyl groups, sulfonamides, hydroxyl, halogen, acetyl, carbamyl, amines and $NO_2$ and combinations thereof and $R_3$ is selected from the group consisting of H and $CH_3$, said compound having a molecular weight of from about 663 to about 775, said amount being effective to protect said mammal upon the reestablishment of flow of fluid to the tissue, said compound being administered in a solution selected from the group consisting of reperfusion solution and cardioplegia solution.

13. A composition for delivering effective amounts of an active compound to a mammal to treat a medical condition caused by the formation or presence of hydroxy free radicals, said composition having the formula:

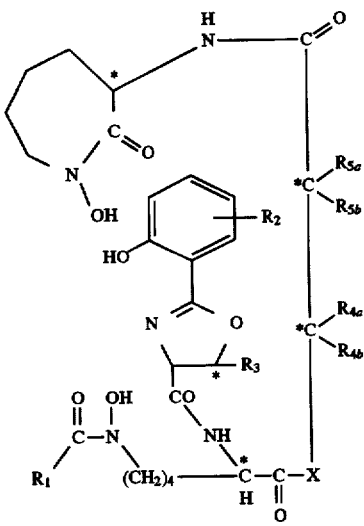

wherein
- $R_1$ is a chemical moiety selected from the group consisting of $(CH_2)_nCH_3$, $(CH_2)_nCOOH$, $(CH_2)_nCOOR$ $(CH_2)_xCH=CH(CH_2)_yCOOH$, $(CH_2)_xCH=CH(CH_2)_yCOOR$ where R is an alkyl group and $(CH_2)_nCONH_2$ where n is from 1 to 7 and x+y is 1 to 5;

$R_2$ is a chemical moiety substituted at any of the 4 open sites on the ring, said chemical moiety being selected from the group consisting of alkyl groups, sulfonamides, hydroxyl, halogen, acetyl, carbamyl, amines and $NO_2$ and combinations thereof;

$R_3$ is a chemical moiety selected from the group consisting of H, $CH_3$ and side chains found on β-hydroxy areinc acids which are capable of forming cyclic oxazoline structures; and $R_{4a}$, $R_{4b}$, $R_{5a}$, $R_{5b}$ are chemical moieties selected from the group consisting of H, alkyl groups and substituted alkyl groups said amount being effective to protect said mammal upon the reestablishment of flow of fluid to an organ within the mammal, said composition being administered in a solution selected from the group consisting of reperfusion solution and cardioplegia solution and x is O, NH, S or $CH_2$.

* * * * *

UNITED STATES PATENT AND TRADEMARK OFFICE
CERTIFICATE OF CORRECTION

PATENT NO. : 5,721,209
DATED : February 24, 1998
INVENTOR(S) : Lawrence D. Horwitz, et al.

It is certified that error appears in the above-identified patent and that said Letters Patent is hereby corrected as shown below:

Column 1, first paragraph, add:

This invention was made in part with government support from a National Institute of Health Grant Numbers AI 33790 and HL 48177.

On the title page:
Item [75], invention address section, correct the states and spelling as follows:

Lawrence D. Horwitz, Engelwood, Colorado;
Marcus A. Horwitz, Los Angeles, California;
Bradford W. Gibson, Berkeley, California;
Joseph Reeve, Oakhurst, California.

Signed and Sealed this

Third Day of November, 1998

Attest:

BRUCE LEHMAN

Attesting Officer

Commissioner of Patents and Trademarks